(12) United States Patent  
Yundt-Pacheco et al.

(10) Patent No.: US 8,589,081 B2  
(45) Date of Patent: Nov. 19, 2013

(54) SYSTEM AND METHOD TO DETERMINE SIGMA OF A CLINICAL DIAGNOSTIC PROCESS

(75) Inventors: John Yundt-Pacheco, Fairview, TX (US); Curtis Parvin, McKinney, TX (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 602 days.

(21) Appl. No.: 12/508,718

(22) Filed: Jul. 24, 2009

(65) Prior Publication Data

US 2011/0022323 A1  Jan. 27, 2011

(51) Int. Cl.
*G01N 33/48* (2006.01)

(52) U.S. Cl.
USPC .......................................................... 702/19

(58) Field of Classification Search
USPC .................. 702/19; 436/89; 600/300, 310
See application file for complete search history.

(56) References Cited

U.S. PATENT DOCUMENTS

| | | | | |
|---|---|---|---|---|
| 5,630,413 A | * | 5/1997 | Thomas et al. | 600/310 |
| 5,687,716 A | * | 11/1997 | Kaufmann et al. | 600/300 |
| 6,273,854 B1 | * | 8/2001 | Kane et al. | 600/300 |
| 6,500,117 B1 | * | 12/2002 | Hancock, Jr. | 600/300 |
| 2006/0194329 A1 | * | 8/2006 | Ogiwara et al. | 436/89 |

* cited by examiner

*Primary Examiner* — Tung S Lau  
*Assistant Examiner* — Xiuquin Sun  
(74) *Attorney, Agent, or Firm* — Stinson Morrison Hecker LLP (57) ABSTRACT

A system and method for determining a sigma of a clinical diagnostic process are disclosed. Specimen data are collected from a plurality of laboratory instruments. The specimen data are evaluated to determine a concentration and an analytical standard deviation for each data point. A clinical diagnostic process is run and patient analyte values are acquired, and a standard deviation is assigned to each patient analyte value based on the standard deviation of specimen data having a corresponding concentration. A single sigma-metric is computed based on the patient analyte assigned standard deviations, the sigma-metric representing the sigma of the clinical diagnostic process. The computed sigma-metric is reported to a user or laboratory manager.

34 Claims, 3 Drawing Sheets

SYSTEM AND METHOD TO DETERMINE SIGMA OF A CLINICAL DIAGNOSTIC PROCESS

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

1. Field of the Invention

The present invention relates to clinical diagnostic processes, and more particularly to a system and method of determining a sigma-metric for such processes.

2. Description of Related Art

The sigma-metric was first introduced by Motorola as part of its Six Sigma Quality Management program. While initially applied to manufacturing processes to reduce defects and improve quality, the six sigma principles are today widely used throughout various aspects of manufacturing and business to improve processes. The sigma-metric defines how many sigmas (i.e., standard deviations) of deviation or variation a process can experience and still be within its allowable tolerance limits. The higher the sigma, the more robust a process is in the presence of error. By definition, a six sigma process is still within specification even with six standard deviations of variation.

Use of the sigma-metric allows quality comparison of widely divergent processes. For example, as cited in the article *Six Sigma Quality Design & Control*, (WI:Westgard QC, Inc., 2001, pg 29), the sigma-metric of various processes are: Airline Baggage Handling—4.2 sigma; Airline Passenger Survival—6.42 sigma; Hematology Specimen Acceptability—4.15 sigma; and Firestone Tires—5 sigma. The author of that article, Dr. Westgard, introduced the six sigma concepts to the clinical diagnostic community with his essay *Six Sigma Quality Management and Desirable Laboratory Precision* (2003, Westgard QC, www.westgard.com/essay35.htm).

Current approaches to computing the sigma of clinical processes assume homoscedasticity—or uniform variance, even though it is widely known that clinical processes are rarely homoscedastic. In fact, it is common in clinical diagnostic processes to have different variation at different concentrations. Because of that variation, using conventional methods of determining sigma-metrics results in multiple sigmas applying to a single clinical process. It is thus unclear which of those sigma (if any) is correct for that clinical process, and how to use the sigma-metric when various sigmas are determined for a single clinical process. Current practice is simply to display the separate sigma for each level of control material.

BRIEF SUMMARY OF THE INVENTION

The present invention addresses the shortcomings of the prior methods of determining and displaying numerous sigmas for the various concentrations encountered in a clinical diagnostic process. The system and method of the present invention allow for determining a single sigma for the process that reflects what is actually experienced by patients getting tested with the clinical process. The result is a single sigma that is applicable to the clinical process that accurately describes the clinical process' actual, in use, error tolerance. Quality control design processes using the sigma output from this invention will have a greater degree of accuracy and control than those that use conventional means.

Exemplary systems and methods for determining a sigma of a clinical diagnostic process and/or processes are disclosed. In use, specimen data are collected from a plurality of laboratory instruments. The specimen data are evaluated to determine a concentration and an analytical standard deviation for each specimen. One or more clinical diagnostic process are run and patient analyte values are acquired, with a standard deviation assigned to each patient analyte value based on the standard deviation of specimen data having a corresponding concentration. A single sigma-metric is computed based on the patient analyte assigned standard deviations, the sigma-metric representing the sigma of the clinical diagnostic process. The computed sigma-metric is reported to a user or laboratory manager for determination of overall system accuracy and usability. The single sigma-metric allows evaluation of multiple laboratory instruments and multiple clinical diagnostic processes (and combinations thereof) to be performed, providing a user or laboratory manager with a single simple metric by which to evaluate the performance of a clinical diagnostic process. Unlike the evaluations of the prior art, there is no uncertainty about whether a particular metric relates to an instrument, a process, or a laboratory, and there is no uncertainty about how or whether those isolated metrics can be combined or interpreted together.

BRIEF DESCRIPTION OF THE DRAWINGS

The present invention will be described in greater detail in the following detailed description of the invention with reference to the accompanying drawings that form a part hereof, in which.

DETAILED DESCRIPTION OF EXEMPLARY EMBODIMENTS

A system and method for determining sigma of a clinical diagnostic process in accordance with exemplary embodiments of the present invention are depicted in FIGS. 1-4. While the invention will be described in detail hereinbelow with reference to the depicted exemplary embodiments and alternative embodiments, it should be understood that the invention is not limited to the specific configurations shown and described in these embodiments. Rather, one skilled in the art will appreciate that a variety of configurations may be implemented in accordance with the present invention. It should be noted that the terms "sigma" and "sigma-metric" are used herein, with "sigma" generally referring to the well-known sigma quality control concept, and "sigma-metric" referring more specifically to a quantity calculated by the system and method for a clinical diagnostic process as described herein.

Figure 1:
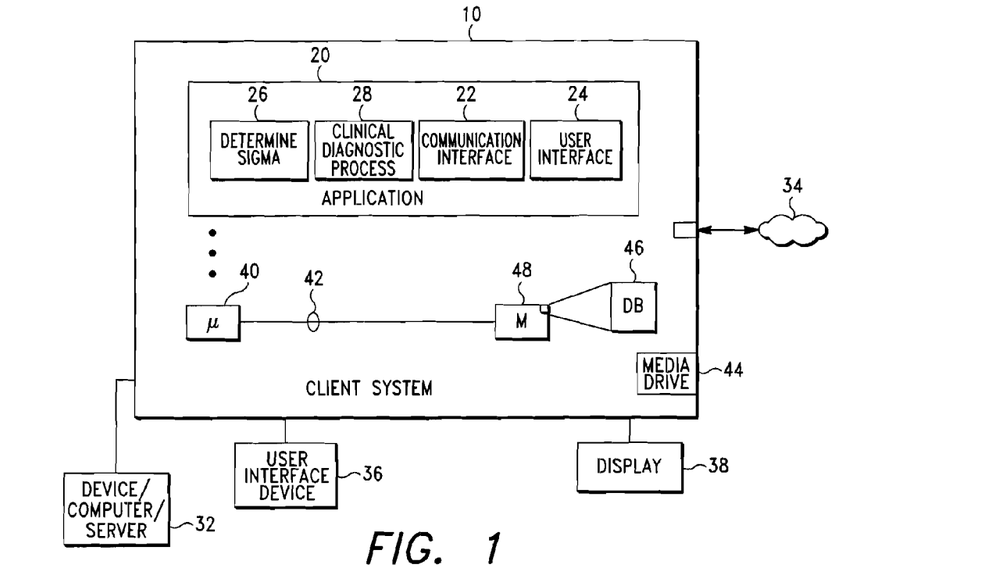
FIG. 1 depicts a block diagram of a client computer system configured with an application module for determining a sigma of a clinical diagnostic process according to a first exemplary embodiment of the present invention.
Figure 2:
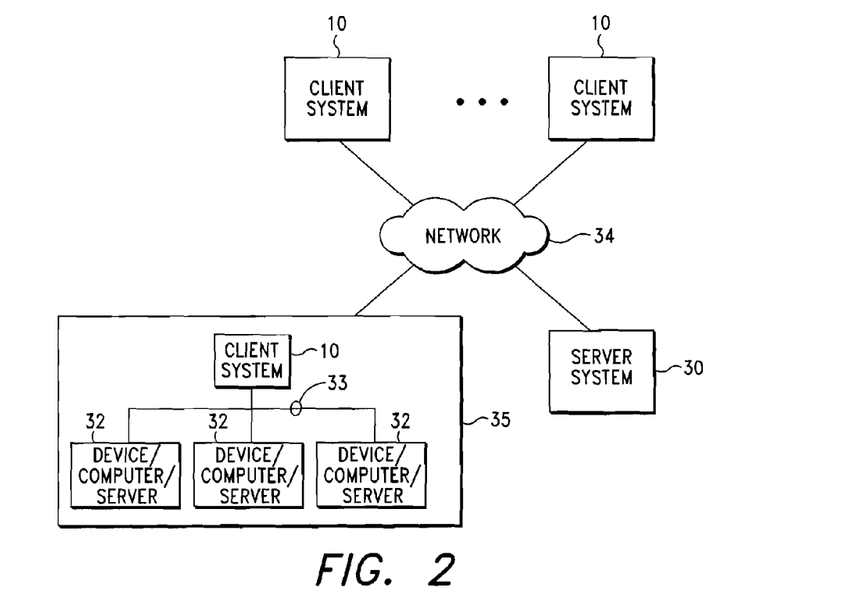
FIG. 2 depicts a block diagram of a network arrangement for executing a shared application and/or communicating data and commands between multiple computing systems and devices according to an exemplary embodiment of the present invention.

Looking first to FIGS. 1 and 2, a system client computer system (e.g., a clinical diagnostic instrument) 10 is configured with an application module 20 operable to perform testing on various analytes, such as patient specimens or quality control specimens. Application module 20 may execute any sequence of diagnostic steps or one or more diagnostic algorithms in conjunction with implementing any clinical diagnostic process, such as a hematology analyzer or any other clinical diagnostic or analytical process. As best shown in FIG. 2, a plurality of client computer systems 10 may be arranged in a network configuration for executing a shared application and/or for communicating data and commands between multiple computing systems and devices according to an exemplary embodiment of the present invention. It should be understood that client computer system 10 may operate as a stand-alone system such as a diagnostic instrument device or laboratory instrument, or it may be connected to a server system 30 and/or other client systems 10 and/or other devices/servers 32 over a network 34.

Several elements in the system depicted in FIGS. 1 and 2 are well-known, existing elements and variations of those exemplary elements may be implemented in accordance with the present invention. For example, client system 10 may include a desktop personal computer, a workstation, a laptop computer, a handheld mobile device, or any other computing device capable of executing the application module 20. In client-server or networked embodiments, client system 10 is configured to interface directly or indirectly with server system 30 over network 34. Network 34 may be any type of network known in the art, such as a local area network (LAN), a wide area network (WAN), the Internet, an ad-hoc network, or any other type of network. Client system 10 may also communicate directly or indirectly with one or more other client systems 10 and devices/servers 32 over network 34. Client system 10 preferably executes a web browsing program, such as Microsoft's Internet Explorer, Netscape Navigator, Opera or the like, allowing a user of client system 10 to access, process and view information and pages available to it from server system 30 or other server systems over network 34. Client system 10 also preferably includes one or more user interface devices 36, such as a keyboard, a mouse, a touch screen, graphical tablet, pen or the like, for interacting with a graphical user interface (GUI) provided on a display 38. Display 38 is preferably a monitor or LCD screen, but may be any type of display device known in the art.

In one exemplary embodiment, application module 20 executes entirely on client system 10 (e.g., stand alone), however, in alternative embodiments the application module may be executed in a networked environment such as a client-server, peer-to-peer, or multi-computer networked environment where portions of the application code may be executed on different portions of the network system or where data and commands are exchanged between various components or devices executing portions of the application code. In local network embodiments, interconnection via a LAN is preferred, however, it should be understood that other networks can be used, such as the Internet or any intranet, extranet, virtual private network (VPN), non-TCP/IP based network, WAN or the like. For example, in the exemplary embodiment depicted in FIG. 2, a LAN 33 interconnects multiple devices to a client system 10. Such a network is exemplary of a multiple instrument environment 35, such as a laboratory or hospital, where multiple instruments, devices, or servers are connected to a client system 10 in a Laboratory Information System (LIS) arrangement. LAN 33 may include wireless and wired links and nodes, and use various communication protocols as are well known in the art.

Preferably, server system 30 acts as a central computer system that executes a majority of, or all, of the application module code, with each client system 10 acting as a terminal or log-in point for a user. For example, client system 10 may reside in a laboratory or a hospital multiple instrument environment 35 as part of a LIS, while server system 30 may reside in a geographically remote location. In such a configuration, the application module code is preferably executed entirely on server system 30, with data and commands sent between client system 10 over network 34. For example, if client system 10 resides in a laboratory, client system 10 would provide the required patient data and/or test results/data, and other information from a local database and local instruments and devices for processing by server system 30, which would then provide processing results back to client system 10, or to other computer systems. It should be understood that the application code may execute entirely on a single system or portions may execute on both systems 10 and 30 (or on multiple systems in other exemplary embodiments) as desired for computational efficiency purposes. Additionally, a client system 10 in a multiple instrument environment 35 may execute a portion or all of the application module code.

Looking again to FIG. 1, in an exemplary embodiment, client system 10 and some or all of its components are operator configurable through operation of the application module 20, which includes computer code executable on a central processing unit 40 coupled to other components over one or more busses 42 as is well known in the art. Computer code, including instructions for operating and configuring client system 10 (or other systems on which the application module is executing, such as server system 30 of FIG. 2) to process data content, monitor and control application processes, and render GUI images as described herein, is preferably stored on a hard disk, but the entire program code, or portions thereof, may also be stored in any other volatile or non-volatile memory medium or device as is well known, such as a ROM or RAM, or provided on any media capable of storing program code, such as a compact disk (CD) medium, digital versatile disk (DVD) medium, a floppy disk, and the like.

An appropriate media drive 44 is provided for receiving and reading documents, data and code from such a computer-readable medium. Additionally, the entire program code of module 20, or portions thereof, or related commands such as Active X commands, may be transmitted and downloaded from a software source, such as server system 30, to client system 10 or from another server system or computing device to client system 10 over the Internet as is well known, or transmitted over any other conventional network connection (e.g., extranet, VPN, LAN, etc.) using any communication medium and protocols (e.g., TCP/IP, HTTP, HTTPS, Ethernet, etc.) as are also well known. It should be understood that computer code for implementing aspects of the present invention can be implemented in a variety of coding languages such as C, C++, Java, Visual Basic, and others, or any scripting language, such as VBScript, JavaScript, Perl or markup languages such as XML, that can be executed on client system 10 and/or in a client server or networked arrangement. In addition, a variety of languages can be used in the external and internal storage of data, e.g., patient results, device and instrument information (e.g., IDs, date/time stamps, calibration information, temperature information, etc.), and other information, according to aspects of the present invention.

In an exemplary embodiment, application module 20 includes instructions for monitoring and controlling clinical diagnostic processes, as well as for providing user interface configuration capabilities, as described herein. Application module 20 is preferably downloaded and stored on media hard drive 44 (or other memory such as a local or attached RAM or ROM), although application module 20 can also be provided on any software storage medium such as a floppy disk, CD, DVD, etc. as discussed above.

In an exemplary embodiment as depicted in FIG. 1, application module 20 includes various software modules for processing data content. A communication interface module 22 is provided for communicating text and/or other data to a display driver for rendering images (e.g., GUI images) on display 38, and for communicating with device/server 32 and/or other computers or server systems in network embodiments. A user interface module 24 is provided for receiving user input, commands, and signals from user interface device 36. Communication interface module 22 preferably includes a browser application, which may be the same browser as the default browser configured on client system 10 as described previously, or any other browser or user interface application. Alternatively, interface module 22 includes the functionality to interface with a browser application executing on client system 10.

Application module 20 also includes a clinical diagnostic process module 28 that performs instructions to process data according to one or more predefined clinical diagnostic processes. For example, the clinical diagnostic process may implement a complete hematology analyzer, a specific glucose analyzer, or any other clinical analytical or diagnostic process, or any variations or combinations of those or other processes. In addition, application module 20 may include other modules operable to perform other clinical diagnostic processes or analyses or quality control processes. As will be explained in more detail below, application module 20 further includes a Determine Sigma module 26 operable to calculate a sigma value or sigma-metric for any or all of the clinical diagnostic process operating in the application module.

Note that while the Determine Sigma module 26 is shown as operating in conjunction with the application module 20 and in conjunction with the clinical diagnostic process 28 (or processes) executing within that module, it should be understood that the determine sigma module is not necessarily itself a part of the application process, but may operate independently of that process. Thus, while the module embodying the determine sigma process of the present invention may be included in an instrument or system implementing a clinical diagnostic process and may execute on a system in conjunction with that process (as depicted in the exemplary system of FIG. 1), or may even be coded into a single executable application with that process, the determine sigma process of the present invention may also be used or implemented in conjunction with other clinical diagnostic processes or in a stand-alone configuration, that is contemplated by and within the scope of the present invention.

Compiled statistics (e.g., device and instrument information), patient information, and other information are preferably stored in database 46, which may reside in memory 48, in a memory card or other memory or storage system such as an attached storage subsystem RAID drive system, for retrieval by the clinical diagnostic process module 28, the determine sigma module 26, and other parts of application module 20. It should be appreciated that application module 20, or portions thereof, as well as appropriate data can be downloaded to and executed on client system 10.

Figure 3:
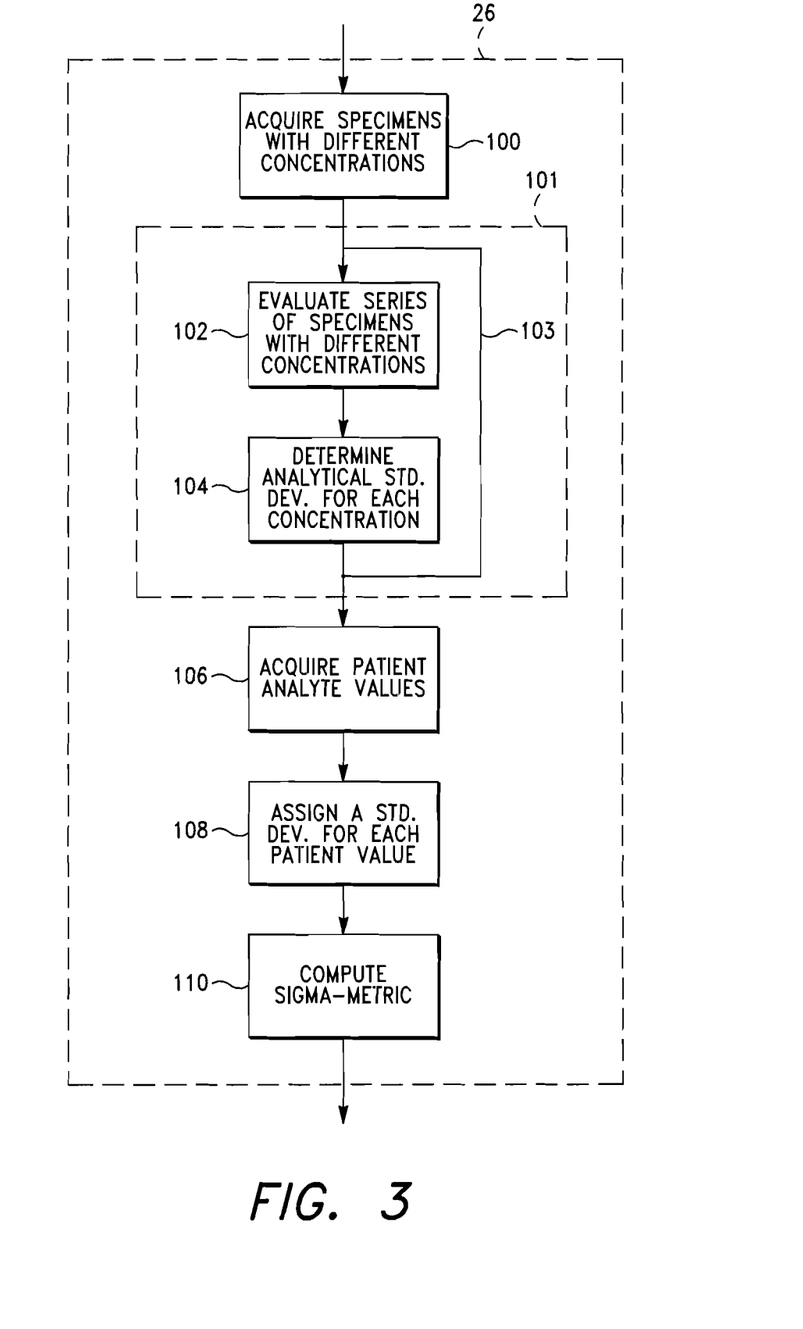
FIG. 3 depicts a block diagram of a process for determining a sigma-metric of a clinical diagnostic process according to an exemplary embodiment of the present invention.
Figure 4:
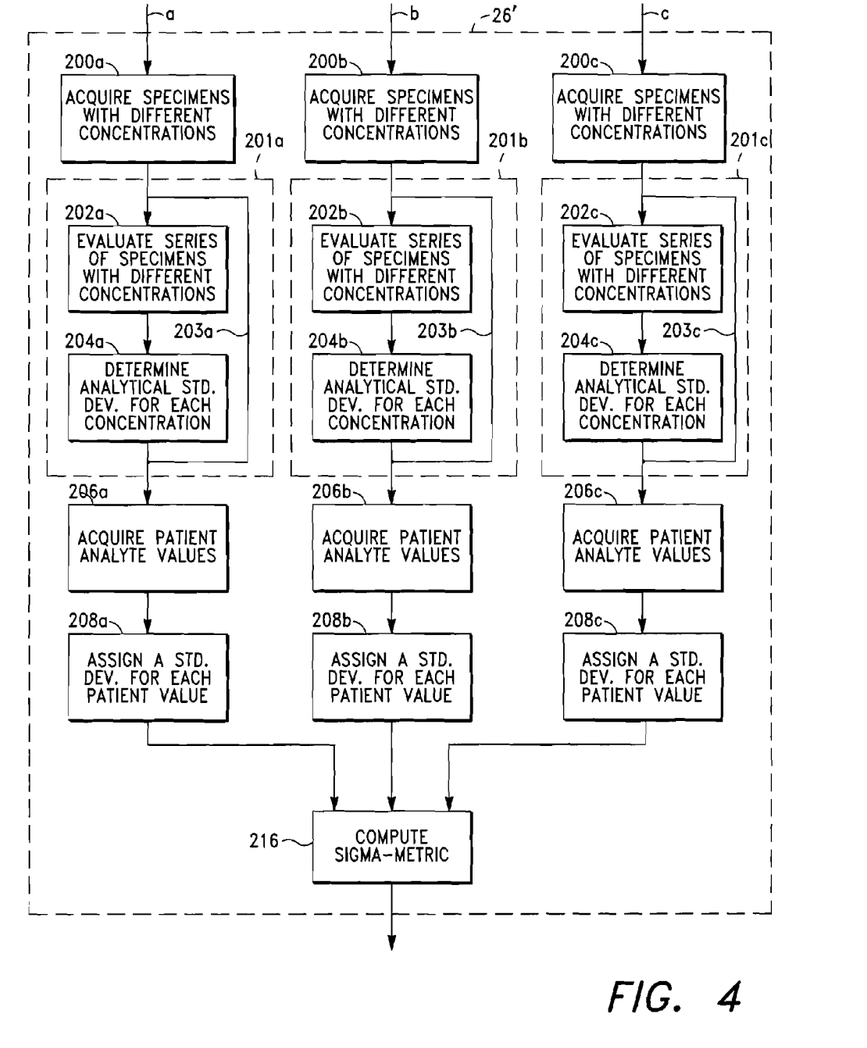
FIG. 4 depicts a block diagram of a process for determining a sigma-metric for a plurality of clinical diagnostic processes according to an exemplary embodiment of the present invention.

The operation of the determine sigma module 26 will now be described with particular reference to FIGS. 3 and 4, depicting exemplary embodiments of the system and process for use with an individual clinical diagnostic process or with a group of clinical diagnostic processes, such as a multi-laboratory environment.

Individual Clinical Diagnostic Process

Turning first to FIG. 3, a method for determining sigma for an individual clinical diagnostic process running on a single laboratory instrument is depicted generally by numeral 26, corresponding to the determine sigma module of system 10 as just described for FIG. 1. Beginning at block 100, the determine sigma process acquires specimens for precision analysis. The specimens may be commercial control materials or may be pooled patient specimens, in either case the sample volumes of the specimens are preferably large enough to allow a precision evaluation to be conducted. Because the accuracy of the calculated sigma is related to the number of samples of each specimen and the range of the specimen concentrations evaluated, most preferably the specimen concentrations cover the entire analytical range of the process being evaluated, and the specimens are repeatedly measured over an extended period of time.

The analytical precision of the repeatedly measured specimens may be determined for each laboratory instrument by various protocols, any of which may be used in conjunction with the present invention. For example, one recommended protocol is described in the publication: *Estimates of Within-Device (or Within-Laboratory) Precision from Evaluation of Precision Performance of Quantitative Methods; Approved Guideline*—(Second Edition, ISBN 1-56238-542-9).

With the specimen data acquired, at block 101 the acquired specimen data are evaluated. At blocks 102 and 104 a series comprising N samples of the acquired specimen data are evaluated for each laboratory instrument in order to estimate the mean and standard deviation (SD) at each specimen concentration. For each laboratory instrument the analytical standard deviations (SDs) for the process at each concentration provided from the evaluation are stored as a set of tuples each comprising a concentration and a corresponding standard deviation (e.g., as (concentration, SD)), with the concentrations preferably spanning the analytical range of the process and the SDs corresponding to an estimate of the analytical imprecision of the process at the corresponding concentration.

With the tuples for the specimen data calculated, the process proceeds to block 106 where the calculated analytical standard deviations are applied to a representative sample of patient analyte values. At block 106, the patient analyte values are acquired. For most analytes, the patient values are preferably taken over an extended period of time, other less-tested analytes may require data collected over a longer timeframe. Most preferably, the patient values reflect the distribution of patient analyte concentrations normally encountered by the clinical diagnostic process.

As described above, the system and method of determining sigma of a clinical diagnostic process of the present invention may be used in conjunction with any clinical diagnostic process. Preferably, the patient values used at block 106 are derived from the clinical diagnostic process for which sigma is being calculated. However, if patient values for that specific clinical diagnostic process are not available then a reference population may be substituted as an estimate of actual patient population that the clinical process evaluates. At block 106, the frequency of occurrence of individual analyte concentrations encountered by the clinical diagnostic process are compiled.

With the SDs of the specimens calculated and the frequency of occurrence of concentrations in the patient data encountered by the clinical diagnostic process compiled, the process proceeds to block 108, where a standard deviation is assigned to each patient value as will now be described.

For each value in the patient data, the concentration of that patient sample is compared to the concentrations in the specimen tuples (concentration, SD) for the laboratory instrument on which the patient value was obtained. When there is a direct match between the patient concentration and a concentration in the tuples, the corresponding SD from the tuple is assigned to that patient sample. Note that a direct match may be considered either an exact match of concentrations, or a match within a predetermined threshold (e.g., if the patient concentration is within 0.1 percent of the concentration in the specimen data). When a patient concentration does not directly match any of concentrations represented in the tuples, the SDs for the patient data are calculated by interpolating or extrapolating from the SDs in the tuples as follows:

When a patient concentration falls between the concentrations of two tuples, (where the lower concentration tuple is designated ($conc_0$, $SD_0$) and the higher concentration tuple is designated ($conc_1$, $SD_1$) the SD for the patient data ($SD_p$) is calculated as $SD_p = SD_0 + (\text{concentration} - conc_0) * (SD_1 - SD_0)/(conc_1 - conc_0)$.

When a patient concentration falls below the lowest (concentration, SD) tuple, designated ($conc_l$, $SD_l$), the SD value of that lowest concentration tuple is assigned to the patient SD, as $SD_p = SD_l$.

Finally, when a patient concentration is higher than the highest (concentration, SD) tuple, designated ($conc_h$, $SD_h$) the value of the assigned patient SD is calculated as $SD_p = (SD_h/conc_h) * (\text{patient concentration})$.

Thus, for each patient value, a SD is assigned based on either a direct match with the specimen data concentrations, by interpolating between specimen values, or by extrapolating from specimen values. It should be understood that while a simple piecewise linear interpolation function and lower limit truncation function have been described, other interpolation and extrapolation schemes may of course be implemented in accordance with the present invention.

At the completion of block 108, each patient value has thus been assigned a SD, with a set of (concentration, SD) tuples representing the SD for each concentration of patient data in a manner similar to that of the specimen data as discussed above.

Total Allowable Error ($TE_A$) goals for a given analyte are the limits of allowable error (expressed in concentration units), defined over the analytical range of the clinical diagnostic process, typically set by a laboratory director or manager. While there are general considerations and guidelines to determine a Total Allowable Error for an analyte, there are no universal or standard total allowable error specifications available. Thus, any given laboratory, group of laboratories, or instruments within a laboratory may use a different $TE_A$ value as determined by the laboratory director. Some guidelines for determining a total allowable error are discussed in the *Stockholm Consensus Conference on Quality Specifications in Laboratory Medicine,* 25-26 Apr. 1999, and in a consensus statement (*Consensus Agreement*: D. Kenny, C. G. Fraser, P. Hyltoft Petersen, A. Kallner; pg 585, Volume 59, No. 7, November 1999, The Scandinavian Journal of Clinical & Laboratory Investigation, Scandinavian University Press, Oslo), which identify what should be considered in determining Total Allowable Error values.

Proceeding to block 110, with the patient data (concentration, SD) tuples compiled, a sigma value for each patient value is estimated by computing the ratio of the Total Allowable Error ($TE_A$) goal for each patient value divided by the SD for the patient value. The estimated sigma-metric for the clinical diagnostic process is calculated by adding the sigma values for each of the patient values and dividing that sum by the total number of patient values.

Because bias is often an issue in laboratory instruments and laboratory testing, the calculation of the sigma-metric can also account for bias by subtracting the bias at each patient value from the Total Allowable Error for the patient value before dividing by the SD for the patient value. As is known in the art, bias can be estimated from proficiency testing program, inter-laboratory quality control programs, or between test methods using patient samples as described in *Method Comparison and Bias Estimation Using Patient Samples; Approved Guideline—Second Edition*. (CLSI document EP9-A2, ISBN 1-56238-472-4).

The sigma-metric as just calculated thus provides a single sigma value representative of the sigma of the entire clinical diagnostic process. Thus, the system and method of the present invention avoid the drawbacks of the prior art in providing concentration dependent sigma values, and allow a sigma for the entire diagnostic process to be considered. The calculated sigma-metric is reported to a laboratory manager and/or other user(s) of the laboratory instruments who can thus make a determination of the quality or validity of the entire clinical diagnostic process. For example, a high sigma-metric generally indicates that a process is working well and there does not need to be much effort expended to ensure that it's functioning correctly. Conversely, a low sigma may indicate that the process is problematic and may not really be providing useful results. Prior to the present invention, there was no effective way to make such a determination.

Groups of Clinical Diagnostic Processes

In a manner similar to that just described for a single instrument, the sigma-metric for a group of clinical diagnostic processes can also be calculated.

Turning to FIG. 4, a method for determining sigma for a group of clinical diagnostic processes running on a plurality of laboratory instruments in a plurality of laboratories is depicted generally by numeral 26'. The processes and laboratories may be geographically dispersed, with communication between the instruments and computer systems as previously described. Block 26' corresponds generally to the determine sigma module 26 as described above for a single clinical diagnostic process. As seen in FIG. 4, three separate clinical diagnostic processes are designated generally as a, b, and c. The steps of determining a sigma-metric for all of the processes is initially the same in all three paths, with the paths combining once the standard deviations are assigned to the patient analyte values as will now be described. It should be apparent that the general flow and steps in each path (i.e., for each clinical diagnostic process) are substantially the same as described above for a single clinical diagnostic process, thus reference to the previous description will facilitate the explanation of this embodiment.

Looking first to blocks 200a, 200b, and 200c, specimens for each process are acquired for analysis. The specimens may be commercial control materials or may be patient specimens, in either case the sample volumes of the specimens are preferably large enough to allow a precision evaluation to be conducted. Because the accuracy of the calculated sigma is related to the number of samples of each specimen and the range of the specimen concentrations evaluated, most preferably, the specimen concentrations cover the entire analytical range of the process being evaluated and the specimens are repeatedly measured over an extended period of time, with the analytical precision of the specimens being determined as previously described.

With the specimen data acquired, at blocks 201a, 210b, and 201c the acquired specimen data are evaluated. At blocks 202a, b, c and 204a, b, c, a series comprising N samples of the acquired specimen data are evaluated for each laboratory instrument in order to estimate the mean and standard deviation (SD) at each specimen concentration. For each laboratory instrument the analytical standard deviations (SDs) for the process at each concentration provided from the evaluation are stored as a set of tuples each comprising a concentration and a corresponding standard deviation (e.g., as: (concentration, SD)), with the concentrations preferably spanning the analytical range of the process and the SDs corresponding to an estimate of the analytical imprecision of the process at the corresponding concentration.

With the tuples for the specimen data calculated, the process paths proceed to blocks 206a, 206b, and 206c, where the calculated analytical standard deviations are applied to a representative sample of patient analyte values. At blocks 206a, b, c, the patient analyte values are acquired. For most analytes, the patient values are preferably taken over an extended period of time, other less-tested analytes may require data collected over a longer timeframe. Most preferably, the patient values reflect the distribution of patient analyte concentrations normally encountered by the clinical diagnostic process and the relative distribution of patient specimens among the plurality of laboratory instruments and laboratories.

As described above, the system and method of determining sigma of a clinical diagnostic process of the present invention may be used in conjunction with any clinical diagnostic process. Preferably, the patient values used at block 206a, b, c are derived from the clinical diagnostic process for which sigma is being calculated. However, if patient values for that specific clinical diagnostic process are not available then a reference population may be substituted as an estimate of actual patient population that the clinical process evaluates. At blocks 206a, b, c, the frequency of occurrence of individual analyte concentrations encountered by the clinical diagnostic process are compiled.

With the SDs of the specimens calculated and the frequency of occurrence of concentrations in the patient data encountered by each of the clinical diagnostic processes (paths a, b, and c) compiled, the processes proceed to blocks 208a, 208b, and 208c where a standard deviation is assigned to each patient value as will now be described.

For each value in the patient data, the concentration of that patient sample is compared to the concentrations in the specimen tuples (concentration, SD) for the laboratory instrument on which the patient value was obtained. When there is a direct match between the patient concentration and a concentration in the tuples, the corresponding SD from the tuple is assigned to that patient sample. Note that a direct match may be considered either an exact match of concentrations, or a match within a predetermined threshold (e.g., if the patient concentration is within 0.1 percent of the concentration in the specimen data). When a patient concentration does not directly match any of concentrations represented in the tuples, the SDs for the patient data are calculated by interpolating or extrapolating from the SDs in the tuples as follows:

When a patient concentration falls between the concentrations of two tuples, (where the lower concentration tuple is designated (conc$_0$ SD$_0$) and the higher concentration tuple is designated (conc$_1$, SD$_1$) the SD for the patient data (SD$_p$) is calculated as SD$_p$=SD$_0$+(concentration−conc$_0$)*(SD$_1$−SD$_0$)/(conc$_1$−conc$_0$).

When a patient concentration falls below the lowest (concentration, SD) tuple, designated (conc$_l$, SD$_l$), the SD value of that lowest concentration tuple is assigned to the patient SD, as SD$_p$=SD$_l$.

Finally, when a patient concentration is higher than the highest (concentration, SD) tuple, designated (conc$_h$, SD$_h$) the value of the assigned patient SD is calculated as SD$_p$=(SD$_h$/conc$_h$)*(patient concentration).

Thus, for each patient value, a SD is assigned based on either a direct match with the specimen data concentrations, by interpolating between specimen values, or by extrapolating from specimen values. It should be understood that while a simple piecewise linear interpolation function and lower limit truncation function have been described, other interpolation and extrapolation schemes may of course be implemented in accordance with the present invention.

At the completion of blocks 208a, b, c, each patient value has thus been assigned a SD, with a set of (concentration, SD) tuples representing the SD for each concentration of patient data in a manner similar to that of the specimen data as discussed above.

With the patient data (concentration, SD) tuples compiled for each of the process paths (a, b, and c), a sigma value for each patient value is estimated by computing the ratio of the Total Allowable Error (TE$_A$) goal for each patient value divided by the SD for the patient value. As described above, bias can be accounted for by subtracting the bias from the Total Allowable Error before dividing by SD. The estimated sigma-metric for the combined clinical diagnostic processes is calculated by adding the sigma values for each of the patient values and dividing that sum by the total number of patient values in the entire population of patient values.

The sigma-metric as just calculated thus provides a single sigma value representative of the sigma of three separate clinical diagnostic processes. The calculated sigma-metric is reported to a laboratory manager and/or other user(s) of the laboratory instruments who can thus make a determination of the quality or validity of the entire clinical diagnostic processes. It should be apparent that while three separate clinical diagnostic processes are depicted in the exemplary embodiment of FIG. 4, the present invention may be applied to any number of such processes, and is not limited by the exemplary embodiment described. It should also be apparent that the features described herein and limitations in the claims hereto may permissibly be combined or arranged in various combinations and embodiments, such embodiments are contemplated by the present invention.

Any quantitative representation presented herein which could permissibly vary without resulting in a change in the basic function to which it is related may permissibly vary from that if the variance does not materially alter the capability of the invention.

While the present invention has been described and illustrated hereinabove with reference to various exemplary embodiments, it should be understood that various modifications could be made to these embodiments without departing from the scope of the invention. Therefore, the invention is not to be limited to the exemplary embodiments described and illustrated hereinabove, except insofar as such limitations are included in the following claims.

What is claimed and desired to be secured by Letters Patent is as follows:

1. A computer-implemented method of determining sigma of a clinical diagnostic process, comprising:
   acquiring specimen data from a plurality of laboratory instruments;
   evaluating said specimen data and determining an analytical standard deviation for a plurality of said specimen data, wherein said analytical deviation corresponds to analytical imprecision in said evaluation;
   acquiring patient analyte values;
   assigning a standard deviation to said patient analyte values based on said specimen data analytical standard deviations;
   computing a single sigma-metric from said assigned standard deviations, wherein said single sigma-metric defines a number of process standard deviations said clinical diagnostic process can experience while remaining within allowable tolerance limits, said sigma-metric representing a sigma for said clinical diagnostic process; and
   reporting said sigma-metric to a user of at least one of said plurality of laboratory instruments.

2. The computer-implemented method of claim 1, wherein said evaluating said specimen data comprises:
   identifying a concentration of each of said specimen data;
   selecting a representative specimen data for specimen data having similar concentrations;
   compiling a series of data comprising a plurality of specimen data having dissimilar concentrations; and
   determining a standard deviation for each specimen data within said series of data.

3. The computer-implemented method of claim 1, wherein said assigning a standard deviation to said patient analyte values comprises:
   determining a concentration of each of said patient analyte values;
   comparing said concentrations of said patient analyte values to concentrations of said specimen data; and
   assigning a standard deviation to said patient analyte values from specimen data having a corresponding concentration.

4. The computer-implemented method of claim 3, wherein assigning a standard deviation comprises:
   matching a concentration of said specimen data to a concentration of said patient analyte value and assigning said specimen data standard deviation to said patient analyte value;
   interpolating a standard deviation for a patient analyte concentration falling between two specimen data concentrations;
   extrapolating a standard deviation for a patient analyte concentration falling below or above the lowest or highest, respectively, specimen data concentrations; and combinations thereof.

5. The computer-implemented method of claim 1, wherein said computing a single sigma-metric comprises:
   applying an averaging function to said patient value assigned standard deviations to determine an estimated standard deviation for said clinical process; and
   dividing a total allowable error for said clinical process by said estimated standard deviation to determine a sigma-metric.

6. The computer-implemented method of claim 5, wherein said averaging function comprises calculating an arithmetic mean of said patient value assigned standard deviations.

7. The computer-implemented method of claim 5, wherein said averaging function comprises calculating an arithmetic median of said patient value assigned standard deviations.

8. The computer-implemented method of claim 5, wherein said total allowable error includes a correction for bias.

9. The computer-implemented method of claim 1, wherein said specimen data comprises data collected over an extended period of time.

10. The computer-implemented method of claim 9, wherein said extended period of time is greater than one year.

11. The computer-implemented method of claim 1, wherein said reporting comprises generating an alert, providing a written report, providing an electronic report, transmitting data, and combinations thereof.

12. A computer-implemented method of determining sigma of a clinical diagnostic process, comprising:
   acquiring specimen data from a plurality of laboratory instruments;
   evaluating said specimen data and identifying a series of data corresponding to specimens having dissimilar concentrations;
   determining an analytical standard deviation for each of said dissimilar concentrations in said series of data, wherein said analytical deviation corresponds to analytical imprecision in said evaluating;
   computing a single sigma-metric from said analytical standard deviations, wherein said single sigma-metric defines a number of process standard deviations said clinical diagnostic process can experience while remaining within allowable tolerance limits; and
   reporting said sigma-metric to a user of at least one of said plurality of laboratory instruments.

13. The computer-implemented method of claim 12, wherein said assigning a standard deviation to said patient analyte values comprises:
   determining a concentration of each of said patient analyte values;
   comparing said concentrations of said patient analyte values to concentrations of said specimen data; and
   assigning a standard deviation to said patient analyte values from specimen data having a corresponding concentration.

14. The computer-implemented method of claim 12, wherein said computing a single sigma-metric comprises:
   applying an averaging function to said patient value assigned standard deviations to determine an estimated standard deviation for said clinical process; and
   dividing a total allowable error for said clinical process by said estimated standard deviation to determine a sigma-metric.

15. The computer-implemented method of claim 14, wherein said total allowable error includes a correction for bias.

16. A system for determining sigma of a clinical diagnostic process, comprising:
   a plurality of laboratory instruments implementing a clinical diagnostic process and operable to acquire data related to that process; and
   a computer system operable to communicate with and receive data from said plurality of laboratory instruments, said computer system having a processor operable to:
      acquire specimen data from said laboratory instruments;
      evaluate said specimen data and determine an analytical standard deviation for a plurality of said specimen data, wherein said analytical deviation corresponds to analytical imprecision in said evaluation;

acquire patient analyte values from said laboratory instruments;
assign a standard deviation to said patient analyte values based on said specimen data analytical standard deviations; and
compute a single sigma-metric from said assigned standard deviations, wherein said single sigma-metric defines a number of process standard deviations said clinical diagnostic process can experience while remaining within allowable tolerance limits, said sigma-metric representing a sigma for said clinical diagnostic process.

17. The system of claim 16, wherein evaluating said specimen data comprises:
identifying a concentration of each of said specimen data;
selecting a representative specimen data for specimen data having similar concentrations;
compiling a series of data comprising a plurality of specimen data having dissimilar concentrations; and
determining a standard deviation for each specimen data within said series of data.

18. The system of claim 16, wherein assigning a standard deviation to said patient analyte values comprises:
determining a concentration of each of said patient analyte values;
comparing said concentrations of said patient analyte values to concentrations of said specimen data; and
assigning a standard deviation to said patient analyte values from specimen data having a corresponding concentration.

19. The system of claim 18, wherein assigning a standard deviation comprises:
matching a concentration of said specimen data to a concentration of said patient analyte value and assigning said specimen data standard deviation to said patient analyte value;
interpolating a standard deviation for a patient analyte concentration falling between two specimen data concentrations;
extrapolating a standard deviation for a patient analyte concentration falling below or above the lowest or highest, respectively, specimen data concentrations; and
combinations thereof.

20. The system of claim 16, wherein computing a single sigma-metric comprises:
applying an averaging function to said patient value assigned standard deviations to determine an estimated standard deviation for said clinical process; and
dividing a total allowable error for said clinical process by said estimated standard deviation to determine a sigma-metric.

21. The system of claim 20, wherein said averaging function comprises calculating an arithmetic mean of said patient value assigned standard deviations.

22. The system of claim 21, wherein said averaging function comprises calculating an arithmetic median of said patient value assigned standard deviations.

23. The system of claim 20, wherein said total allowable error includes a correction for bias.

24. A computer-readable medium having computer-executable instructions for performing a method of determining sigma of a clinical diagnostic process, the method comprising:
acquiring specimen data from a plurality of laboratory instruments;
evaluating said specimen data and determining an analytical standard deviation for a plurality of said specimen data, wherein said analytical deviation corresponds to analytical imprecision in said evaluation;
acquiring patient analyte values;
assigning a standard deviation to said patient analyte values based on said specimen data analytical standard deviations;
computing a single sigma-metric from said assigned standard deviations, wherein said single sigma-metric defines a number of process standard deviations said clinical diagnostic process can experience while remaining within allowable tolerance limits, said sigma-metric representing a sigma for said clinical diagnostic process; and
reporting said sigma-metric to a user of at least one of said plurality of laboratory instruments.

25. The computer-readable medium of claim 24, wherein said evaluating said specimen data comprises:
identifying a concentration of each of said specimen data;
selecting a representative specimen data for specimen data having similar concentrations;
compiling a series of data comprising a plurality of specimen data having dissimilar concentrations; and
determining a standard deviation for each specimen data within said series of data.

26. The computer-readable medium of claim 24, wherein said assigning a standard deviation to said patient analyte values comprises:
determining a concentration of each of said patient analyte values;
comparing said concentrations of said patient analyte values to concentrations of said specimen data; and
assigning a standard deviation to said patient analyte values from specimen data having a corresponding concentration.

27. The computer-readable medium of claim 26, wherein assigning a standard deviation comprises:
matching a concentration of said specimen data to a concentration of said patient analyte value and assigning said specimen data standard deviation to said patient analyte value;
interpolating a standard deviation for a patient analyte concentration falling between two specimen data concentrations;
extrapolating a standard deviation for a patient analyte concentration falling below or above the lowest or highest, respectively, specimen data concentrations; and
combinations thereof.

28. The computer-readable medium of claim 24, wherein said computing a single sigma-metric comprises:
applying an averaging function to said patient value assigned standard deviations to determine an estimated standard deviation for said clinical process; and
dividing a total allowable error for said clinical process by said estimated standard deviation to determine a sigma-metric.

29. The computer-readable medium of claim 28, wherein said averaging function comprises calculating an arithmetic mean of said patient value assigned standard deviations.

30. The computer-readable medium of claim 28, wherein said averaging function comprises calculating an arithmetic median of said patient value assigned standard deviations.

31. The computer-readable medium of claim 28, wherein said total allowable error includes a correction for bias.

32. The computer-readable medium of claim 24, wherein said specimen data comprises data collected over an extended period of time.

33. The computer-readable medium of claim 32, wherein said extended period of time is greater than one year.

34. The computer-readable medium of claim 24, wherein said reporting comprises generating an alert, providing a written report, providing an electronic report, transmitting data, and combinations thereof.

* * * * *